United States Patent [19]

Tsukada et al.

[11] 4,090,403
[45] May 23, 1978

[54] APPARATUS FOR JUDGING THE USEFUL LIFE OF TOOLS

[75] Inventors: Tameyasu Tsukada, Tokyo; Masaharu Terashima, Yokohama, both of Japan

[73] Assignee: Tokyo Shibaura Electric Co., Ltd., Kawasaki, Japan

[21] Appl. No.: 708,715

[22] Filed: Jul. 26, 1976

Related U.S. Application Data

[63] Continuation of Ser. No. 645,637, Dec. 31, 1975, abandoned.

[30] Foreign Application Priority Data

Nov. 21, 1975 Japan .................................. 50-139989

[51] Int. Cl.² ............................................ G01N 19/00
[52] U.S. Cl. ..................................................... 73/104
[58] Field of Search ................ 73/104, 105; 235/151.3

[56] References Cited

U.S. PATENT DOCUMENTS

| 3,299,697 | 1/1967 | Sparling | 73/104 |
| 3,809,870 | 5/1974 | Auble et al. | 73/104 |
| 3,834,615 | 9/1974 | Watanabe et al. | 73/104 |
| 3,841,149 | 10/1974 | Edwin et al. | 73/104 |

Primary Examiner—Anthony V. Ciarlante
Attorney, Agent, or Firm—Oblon, Fisher, Spivak, McClelland & Maier

[57] ABSTRACT

The apparatus comprises a drill power meter for producing an electric signal representing the drilling resistance of a workpiece, a filter for shaping the waveform of the electric signal, an integrator for integrating the output of the filter, a comparator for comparing the output from the integrator with a reference signal for producing a pulse when the former is larger than the latter, a first counter for counting the pulse, a second counter for counting the total number of measurements of the drilling resistance of the workpiece performed by the drill power meter, and means for comparing the counts of the first and second counters for judging the useful life of the drill.

6 Claims, 14 Drawing Figures

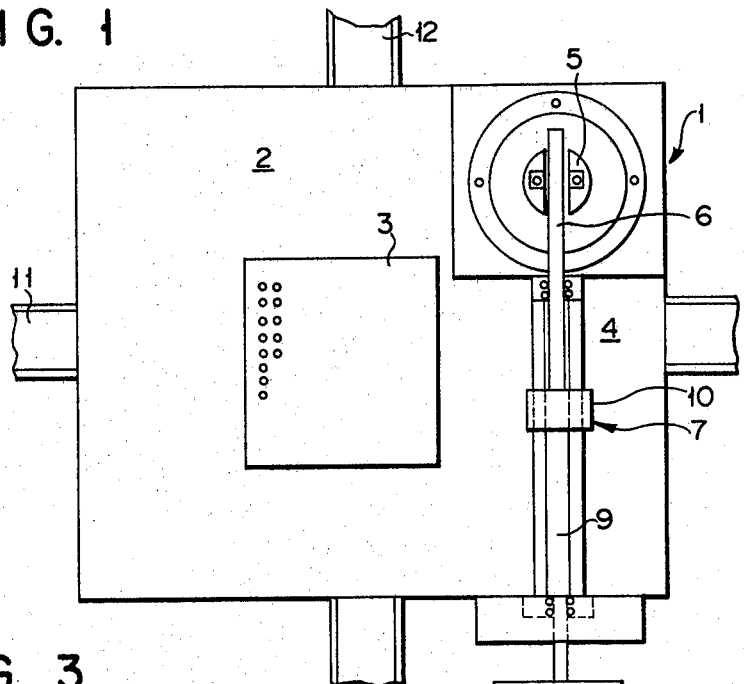
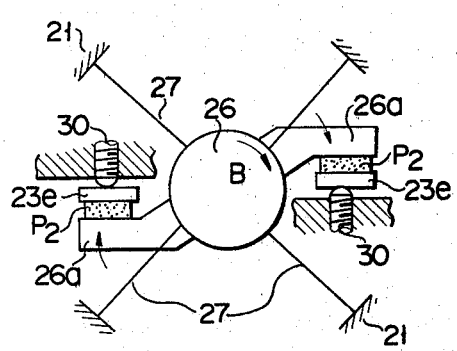
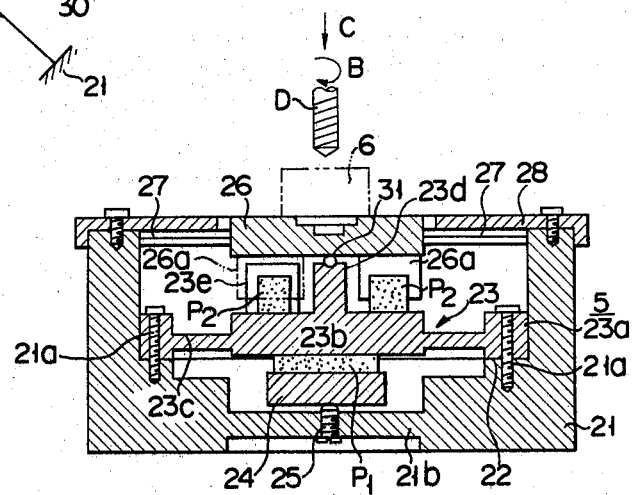

APPARATUS FOR JUDGING THE USEFUL LIFE OF TOOLS

This is a continuation, of application Ser. No. 645,637, filed Dec. 31, 1975 now abandoned.

This invention relates to apparatus for measuring or judging the effective life of a tool for example a drill.

In the manufacture of a laminated print substrate containing a thin copper foil, for example, a number of small openings are formed by using drills. The quality and accuracy of the surface of the laminated substrate after the drilling operation, for example the surface coarseness, and the bonding of resin are greatly influenced by the effective life, that is the degree of wear of the drill. In other words, while the drill is sharp and has an excellent cutting ability, the drilled opening has an excellent quality. However, when the drill wears to some extent, the drilled surface becomes coarse and resin adheres to such coarse surface. To obviate such disadvantages, the number of works that can be made with one drill is often limited to a prescribed number, for example 3000, and when the prescribed working number is reached, the drill is exchanged with a new one. However, the useful life of the drills available on the market differs substantially from one to the other. For example, the useful life of some drills is only 500 works whereas there are some capable of drilling 5000 or more openings. Accordingly, when the life of the drill is administrated by the number of works performed thereby, there is a fear that unsatisfactory laminated print substrates or the like are formed by using worn out or inaccurate drills.

According to another method of judging the life of a drill, the configuration of chips formed by the drilling operation is used as a measure of the useful life. In this method too, the correlation between the life of the drill and the configuration of the chips is not definite. Moreover, as such judgement is usually done by visual observation, the result of judgement is not definite. In this manner, prior art methods of administration of the life of drills are not accurate and require troublesome operations.

Accordingly, it is an object of this invention to provide novel apparatus for judging the effective life of a tool capable of automatically and correctly judging the effective life.

According to this invention there is provided apparatus for judging the useful life of a tool comprising a detector for producing an electric signal corresponding to the working resistance of a workpiece, signal processing means for processing the electric signal, a comparator for producing a pulse signal when the output signal from the signal processing means is different from a predetermined reference signal, a first counter for counting the number of the pulse signals from the comparator, a second counter for counting a predetermined number of measurements of the working resistance performed by the detector, and means for comparing the counts of the first and second counters for judging the useful life of the tool.

This invention can be more fully understood from the following detailed description when taken in conjunction with the accompanying drawings, in which:

FIG. 1 is a plan view showing a drill power meter mounted on a table of a numerically controlled drilling apparatus;

FIG. 2 is a sectional view showing the construction of the drill power meter shown in FIG. 1;

FIGS. 3 and 4 are diagrammatic representations useful to explain the principle of operation of the drill power meter shown in FIG. 2;

Figure 4:
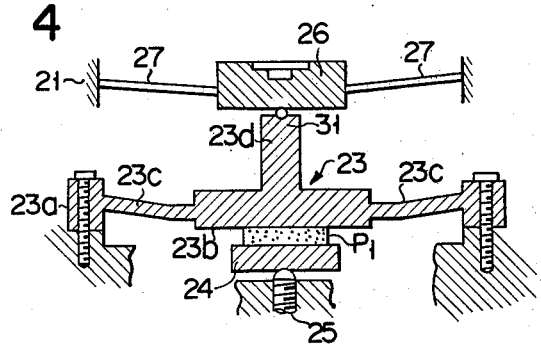

Referring now to the accompanying drawings one embodiment of the invention as applied to a drilling apparatus will be described. The apparatus for judging the effective life of a drill illustrated in the drawing comprises a drill power meter acting as a detector for producing an electrical signal representing the resistance to a drilling operation. The drill power meter is used to generate an electric signal having a voltage proportional to the magnitude of the torque or thrust imparted to the workpiece by the drill during the drilling operation and is mounted on a table 2 of a numerically controlled drilling apparatus 1 as shown in FIG. 1, and a workpiece 3 illustrated as a laminated printed substrate 3 is also mounted on the table 2. The drill power meter 4 comprises a main body 5, and a workpiece feeding device 7 which is used to automatically feed a sample piece 6 having the same construction as the substrate 3. The workpiece feed device 7 comprises a pulse motor 8, a threaded rod 9 driven by the pulse motor 8, and a slider 10 moved by the rotation of the threaded rod 9. When the motor 8 is energized, the slider 10 is moved toward the main body 5 whereby the sample piece 6 is stepwisely advanced at a definite pitch through the main body 5 each time the drilling resistance is measured. The pulse motor 8 is operated according to the program of the numerical control system. For example, the table 2 is moved along X axis 11 and Y axis 12 so as to bring the drill to a position above the main body 5 of the drill power meter 4 when the drill has formed 200 openings through the laminated printed substrate 3. Under these conditions the resistance to the drilling operation through the sample piece 6 is measured for the first time, and when the measurement has completed, the pulse motor is energized by the numerical control system to move sample piece 6 one pitch upwardly. Under these conditions, the second drilling resistance measurement is performed. Such measurements are performed sequentially and when the four drilling resistance measurements are made, the table 2 is moved to bring the drill to the next drilling position of the laminated printed substrate 3 or the drill is exchanged with a new one dependent upon the result of measurement.

The detail of the construction of the main body 5 of the drill power meter 4 will now be described with reference to FIGS. 2 to 4. As shown in FIG. 2 the main body 5 comprises a bottom closed cylindrical housing 21 formed with a shoulder 22 on the inner wall thereof. The periphery 23a of a diaphragm 23 is secured to shoulder 22 by screws 21a. The diaphragm 23 is constructed to have a thick periphery 23a and a thick central portion 23b interconnected by a thin web portion 23c which makes the diaphragm to be flexible in the vertical direction. The central portion 23c is made to be rigid and provided with a projection 23b at its center.

Beneath the central portion 23b of the diaphragm 23 is positioned a flat disc shaped supporting member 24 and a thrust detecting piezoelectric element $P_1$ is interposed therebetween. The supporting member 24 is urged upwardly by a pressure adjusting screw 25 threaded through the bottom wall of the housing 21. The sample piece 6 is supported by a holder 26, the outer periphery thereof being supported by a criss-cross shaped spring 27. This spring is used to support the holder 26 by the housing 21 as shown in FIG. 3. The upper opening of the housing 21 is closed by a suitable cover 28.

A projection 26a is provided for the lower surface of the holder to rotatably receive a projection 23c on the upper surface of the central portion 23b of the diaphragm 23, and a torque detecting piezoelectric element $P_2$ is interposed between the two projections 26a and 23e. As shown in FIG. 3, the adjustment of the prepressure is done by an adjusting screws 30 engaging the projection 23e. A steel ball 31 is interposed between the holder 26 and the top of the projection 23d to assure smooth rotation of the former. Steel ball 31 also acts to transmit the thrust.

The method of measuring the resistance to the drilling operation through the sample piece 6 with the drill power meter described above is as follows. The sample piece 6 is secured on the holder 26 as shown in FIG. 2 and a drill D is moved downwardly as shown by arrow C while it is rotated as shown by arrow B. As the drilling operation is commenced in this manner, a torque and a thrust are applied to the sample piece 6.

Figure 5:
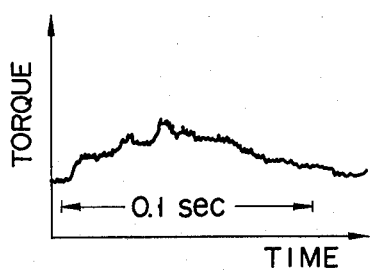
FIGS. 5 and 6 show waveforms of the torque and thrust obtained by the drill power meter shown in FIG. 2.

The direction of the torque is also shown by arrow B (see FIG. 3), and the torque detection piezoelectric element $P_2$ will be clamped between the projection 23e on the diaphragm 23 and the projection 26a on the holder 26. As a result, the piezoelectric element $P_2$ is compressed by a pressure corresponding to the torque acting upon the sample piece 6 so as to produce a corresponding electric signal. By using a sample piece 6 made of the same material as the workpiece it is possible to readily determine the degree of wear or the remaining life of the drill at any time. FIG. 5 shows one example of the waveform of an electric signal showing the torque when an ultra-hard drill having a diameter of 0.8 mm, rotated at a speed of 80000 r.p.m. and fed at a rate of 0.03 mm/revolution is used to form an opening through the laminated printed substrate 1. While the torque is measured the diaphragm 23 acts as a rigid body in the direction of rotation of the drill. The rotational movement of the holder 26 is permitted by the criss-cross shaped spring.

Figure 6:
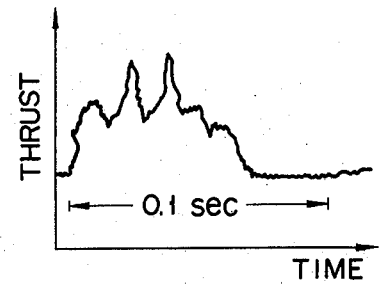

The thrust applied to the sample piece 6 during the drilling operation acts upon the thrust detection piezoelectric element $P_1$ on the supporting member 24 via holder 26, steel ball 31 and diaphragm 23 as shown in FIG. 4. At this time, the holder 26 displaces downwardly while being supported by the criss-cross shaped spring 27 to apply a pressure corresponding to the thrust upon the piezoelectric element $P_1$. At this time, the diaphragm 23 can flex in the vertical direction due to its construction described above. In this manner, the piezoelectric element $P_1$ produces an electric signal corresponding to the thrust acting upon the sample piece 6. FIG. 6 shows one example of a thrust curve obtained under the same condition as the curve shown in FIG. 5.

As has been described hereinabove, it is possible to measure the torque and thrust by the electric signals produced by the piezoelectric elements $P_2$ and $P_1$, and the prepressure adjustments before measurement can be readily made by turning adjusting screws 30 and 25.

As shown in FIG. 1, since the drill power meter which measures the drilling resistance is mounted on the table movable in the X and Y directions it is not necessary to dismount the workpiece from the table each time the useful life of the drill is measured, thus facilitating the measuring operation. Accordingly, it is possible to always form accurate openings which are especially desirable for the working of laminated printed substrate.

Figure 7:
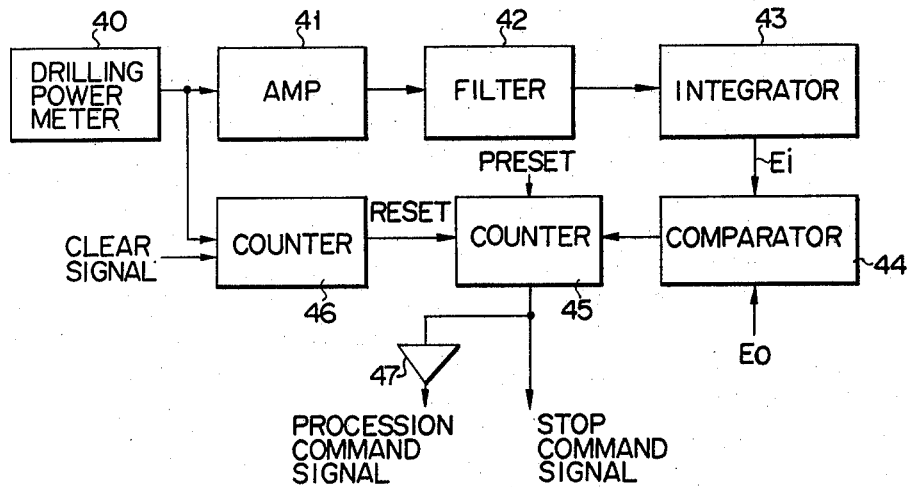
FIG. 7 is a block diagram showing one embodiment of this invention.

Signals from the piezoelectric elements $P_1$ and $P_2$ are applied to an amplifier 41, singly or jointly, as the output from the drill power meter 40, as shown in FIG. 7. It should however, be understood that the drill power meter 40 is not limited to that already described.

Figure 8:
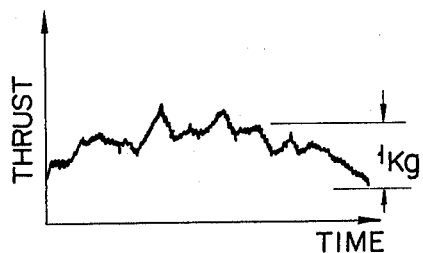
FIGS. 8 through 14 show signal waveforms useful to explain the operation of the apparatus shown in FIG. 7.
Figure 9:
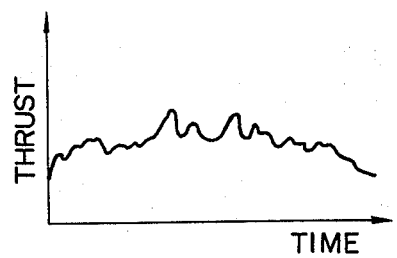
Figure 10:
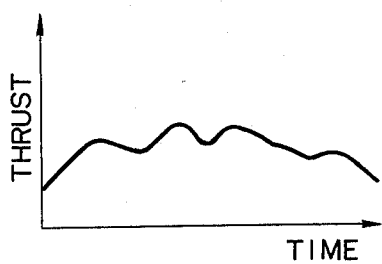

Since the output signal from the drill power meter 40 is of low voltage and contains complicated components inherent to the drilling operation, after amplifying the output signal by amplifier 41, the waveform of the signal is shaped by a filter 42. In the following description, a thrust signal produced by the piezoelectric element $P_1$ is used as the signal for measuring the drilling resistance. After amplification, the thrust signal has a waveform as shown in FIG. 8 and when shaped by the filter its waveform is smoothed as shown by FIG. 9. In the case of FIG. 9, the filter has a cut off frequency of 1,000 Hz, but when a low pass filter having a cut off frequency of 100 Hz is used more smooth waveform as shown in FIG. 10 can be obtained. Of course, the amplification coefficient of the amplifier 41 and the cut off frequency of the filter 42 can be selected to any desired values according to the conditions of application.

The output signal from filter 42 is integrated by an integrator 43 and then applied to one input of a comparator 44. A reference voltage $E_O$ is applied to the other input of the comparator 44 so that it provides an output to a counter 45 when the output $E_i$ from the integrator is larger than the reference voltage $E_O$.

Figure 11:
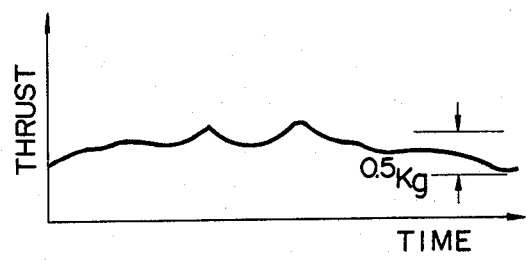
Figure 12:
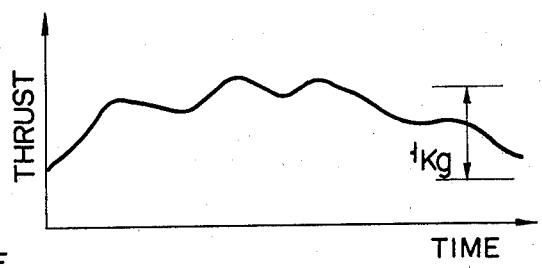
Figure 13:
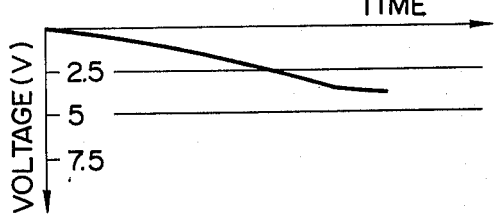
Figure 14:
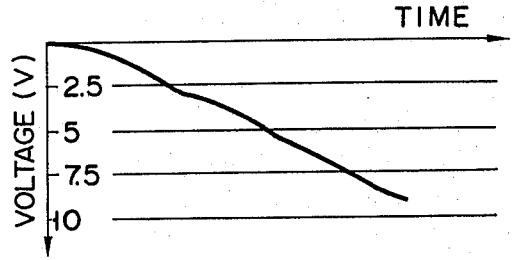

FIGS. 11 and 12 show the relationship between the thrust of a drill and the number of drilling operations. FIG. 11 shows the thrust curve of the first drilling operation showing that the maximum thrust is little above 0.5 kg. However, at the 8000th drilling operation the maximum thrust becomes about 1.2 kg as shown in FIG. 12 meaning that the maximum thrust has increased about two times due to the wear of the drill. These data were obtained with a drill having a diameter of 0.8mm, rotated at a speed of 80,000 r.p.m. and fed at a rate of 0.03mm/revolution. The level of the output voltage $E_i$ from the integrator 43 also varies with the magnitude of the thrust. Thus, when the thrust is small as shown in FIG. 11 the integrator output $E_i$ is also small, for example about 3.5V, as shown in FIG. 13, but as the thrust increases as shown in FIG. 12, the integrator output becomes large, for example about 8.5V as shown in FIG. 14. For this reason, by setting a suitable reference voltage $E_O$, it is possible to produce an output from the comparator 44 when the useful life of the drill has reached and the thrust has exceeded a predetermined value. Although not shown in the drawing, suitable means are provided to vary the reference voltage $E_O$ in accordance with the types of the drill and the workpiece.

The counter 45 comprises a four bit counter preset such that its content becomes 2 and is reset by a carry output from a four bit counter 46 which counts a predetermined number of the drilling resistance measurements in response to the output from the drill power meter 40. The purpose of using the combinations of two counters 45 and 46 is to statistically process varying resistances to drilling operations thus judging the end of the life of the drill in accordance with the ratio of the number of measurements $N_0$ counted by counter 46 to the number of measurements $N_1$ when $E_O < E_i$. Thus, in this example, where the condition $E_O < E_i$ appears more than two times while four mesurements are made, the four bit counter 45 which has been preset to 2 produces a carry output which is used as a signal indicating the end of the drill life for applying a command signal to the numerical control system for stopping the drilling operation and exchanging the drill. If no carry signal is produced by counter 45, a command signal for continuing the drilling operation is sent to the numerical control system through an inverter 47. According to the system shown in FIG. 4 when the results of the first two measurements among the four measurements are $E_O < E_i$ counter 45 produces the carry signal before counter 46 applies a reset signal thus stopping the drilling operation. In such a case, for the purpose of returning the entire system to the condition before commencement of the measurement, a clear signal is sent to counters 45 and 46 from the numerical control system when the drilling operation is stopped or the drill is exchanged.

The measurement of the drilling resistance is performed at each 200the drilling operation, for example, and the drilling operation is continued under control of the numerical control system until the end of the useful life of the drill is reached or the drilling operation of a workpiece has completed.

Although in the foregoing embodiment a drill power meter has been used for measuring the resistance to the drilling operation any measuring means that can detect the variation of a physical quantity such as cutting temperture, and number of revolutions of the driving shaft caused by the wear of the drill in terms of an electric quantity can also be used. The apparatus of this invention can also measure the useful life of any cutting tool, a bite for example. When the apparatus of this invention is combined with a workpiece supply device and a tool exchange device a full automatic drilling machine can be obtained.

It should be understood that the workpiece is not limited to a laminated printed substrate. In any case, the sample piece 6 should be the same material as the workpiece because the sample piece is used to manifest the same working resistance as the workpiece.

What we claim is:

1. An apparatus for judging the useful life of a tool comprising:
    a detector for producing an electric signal corresponding to the working resistance of a workpiece, the detector having a tool power meter integrally provided on a workpiece table movable in the X and Y directions which are perpendicular to each other for producing the electric signal by using a sample made of the same material as the workpiece,
    signal processing means for processing the electric signal,
    a comparator for producing a pulse signal when the output signal from the processing means is different from a predetermined reference signal,
    a first counter for counting the number of pulses from the comparator,
    a second counter for counting a predetermined number of measurements of the working resistance performed by the detector, the output of said second counter being fed to said first counter and
    means for obtaining an output from the first counter for judging the useful life of the tool.

2. An apparatus according to claim 1 wherein said detector further comprises means for stepping the sample each time the useful life of the tool is measured.

3. An apparatus according to claim 1 wherein said detector comprises a tool power meter including a casing, a diaphragm having a rigid central portion, said diaphragm being horizontally disposed at said casing with the periphery thereof secured to the casing, a sample piece holder for supporting a sample piece close to the upper surface of said diaphragm to be rotatable about an axis thereof and to be movable in the vertical direction, a first projection projecting downwardly from said sample piece holder, a second projection projecting upwardly from said diaphragm to confront said first projection, a first piezoelectric element interposed between said first and second projections for detecting the torque, a second piezoelectric element interposed between the casing and the lower surface of said diaphragm.

4. An apparatus according to claim 1 wherein said detector comprises a tool power meter including a cylindrical casing having a closed bottom, a diaphragm having a rigid central portion, said diaphragm being disposed in said casing with the periphery thereof secured to the casing, a sample piece holder for supporting a sample piece close to the upper surface of said diaphragm to be rotatable about an axis thereof and to be movable in the vertical direction, a first projection projecting downwardly from said sample piece holder, a second projection projecting upwardly from said diaphragm to confront said first projection, a first piezoelectric element interposed between said first and a second projections for detecting the torque, second piezoelectric element interposed between the bottom of said casing and the lower surface of said diaphragm.

5. An apparatus according to claim 1 wherein said signal processing means comprises an amplifier for amplifying the electric signal from said detector, a low pass filter for removing the high frequency component of the output from said amplifier, an integrator for integrating the output from said low pass filter each time the measurement is performed, and means for applying the output from said integrator to said comparator.

6. an apparatus for judging the useful life of a tool comprising a detector for producing an electric signal corresponding to the working resistance of a workpiece, signal processing means for processing said electric signal, a comparator for producing a pulse signal when the output signal from said signal processing means is different from a predetermined reference signal, a first counter for counting the number of pulses from said comparator, a second counter for counting a predetermined number of measurements of the working resistance performed by said detector, and means for comparing the counts of said first and second counters for judging the useful life of said tool, said first counter being set to produce a first carry signal at a count corresponding to the total number of measurements during one measuring cycle and preset with a predetermined count, said second counter producing a second carry signal for resetting said first counter when the second counter has counted the total number of measurements of the working resistance of the workpiece, and said judging means comprising means for sending said first carry signal as a work stopping command signal, and an inverter for inverting said first carry signal for producing a work continuing command signal.

* * * * *